United States Patent [19]

Urbas

[11] Patent Number: 4,691,055

[45] Date of Patent: Sep. 1, 1987

[54] CONCENTRATION OF ORGANIC CHEMICALS FROM DILUTE AQUEOUS SOLUTIONS

[75] Inventor: Branko Urbas, Darien, Ill.

[73] Assignee: CPC International Inc., Englewood Cliffs, N.J.

[21] Appl. No.: 327,849

[22] Filed: Dec. 7, 1981

[51] Int. Cl.$^4$ ............................................. C07C 59/08
[52] U.S. Cl. ..................................... 562/589; 562/608
[58] Field of Search ................................. 562/589, 608

[56] References Cited

U.S. PATENT DOCUMENTS

| | | | | |
|---|---|---|---|---|
| 2,422,504 | 6/1947 | Spence | ................................ | 562/589 |
| 3,965,036 | 6/1976 | Himmelstein | ........................ | 562/608 |
| 4,159,223 | 6/1979 | Baierl | ................................ | 562/589 |

FOREIGN PATENT DOCUMENTS

| | | | | |
|---|---|---|---|---|
| 529982 | 9/1956 | Canada | ................................ | 562/608 |
| 332983 | 8/1930 | United Kingdom | ................ | 562/609 |
| 1126315 | 9/1968 | United Kingdom | ................ | 562/608 |

*Primary Examiner*—Paul J. Killos

[57] ABSTRACT

An improved process is provided for concentrating organic compounds from dilute aqueous solutions such as fermentation liquors. Conventional distillation of the compounds to remove the bulk of the water is eliminated by selective adsorption on adsorbent carbon. The compounds are eluted from the carbon with the vapors of a volatile solvent and then the volatile solvent is evaporated from the eluate to give a concentrated aqueous solution containing at least 30% by weight of the organic compounds.

19 Claims, No Drawings

CONCENTRATION OF ORGANIC CHEMICALS FROM DILUTE AQUEOUS SOLUTIONS

FIELD OF THE INVENTION

This invention relates to a method for the concentration of organic chemicals which are present in dilute aqueous solutions such as fermentation liquors.

BACKGROUND OF THE INVENTION

The production of organic chemicals by microorganisms is well known to those familiar with the fermentation art. These chemicals are produced by the microorganisms in dilute aqueous solutions, generally from about 1% to 10% by weight, so that their recovery in pure form involves separation from a large quantity of water. The expense of such separation has been so great that production of these chemicals by fermentation has not been able to compete with their production based on petroleum fossil fuel sources. However, the gradual depletion of petroleum fossil fuel with the resultant increase in prices of petrochemical feedstocks has revived interests in such fermentation reactions which can convert carbohydrates that are renewable raw materials into simple organic chemicals.

For these reasons, it is desirable to develop a low-cost process for seperation of organic chemicals from dilute aqueous solutions. Various methods have been proposed for such separations. These include solvent extraction, freeze crystallization, distillation and selective adsorption.

It is well known that activated carbon selectively adsorbs organic chemicals from aqueous solutions. The adsorbed chemicals can then be desorbed by various techniques such as heating, displacing the adsorbed material with steam or desorbing the material with a solvent. Spence, U.S. Pat. No. 2,422,504, disclosed a process for recovering lower fatty acids from a dilute aqueous solution. This involved first adsorbing the material on activated carbon. Then the carbon was heated to 100° C. under vacuum to remove a part of the water plus some acid. Finally, the acid and remaining water were extracted with a solvent and the solvent and acids were separated. The expensive heating step detracts from this process.

Baieri, Canadian Pat. No. 978,308, disclosed a method for recovering acetic acid and furfural from sulfite waste liquors obtained as a by-product of paper manufacture. In his process, the liquor was passed through a stream stripper and then through a carbon column to adsorb some of the organic chemicals present. The chemicals were subsequently desorbed using a solvent which was at least partially vaporized. Suggested solvents were the lower alcohols, acetone, benzene, and ether. However, the examples were directed to the recovery of acetic acid with an alcohol which gave an ester or mixtures of ester, alcohol and acid. The mixed product made this process unattractive.

Baieri, U.S. Pat. No. 4,016,180, disclosed a two-stage adsorption-desorption process for concentrating sulfite waste liquors. The liquors are passed through a carbon column to adsorb the organic chemicals. A more concentrated solution of the chemicals was then obtained by the use of either steam or a solvent to desorb the material. Examples include the use of steam, methanol or ethanol to remove acetic acid from the carbon. When alcohols were used as desorbents, mixtures containing esters were obtained. The process described by Baieri requires quite complex equipment with both upflow and downflow of the eluting solvent.

We have now discovered a greatly simplified adsorption process for the concentration of organic compounds from dilute aqueous solutions which is energy-efficient and which permits the use of simple equipment. This process is particularly suitable for the concentration of organic compounds obtained by microbial fermentations.

SUMMARY OF THE INVENTION

In accordance with the present invention, there is provided a process for concentrating a dilute aqueous solution of an organic compound. The organic compound is adsorbed on adsorbent carbon and then eluted from the carbon with a volatile solvent before the volatile solvent is separated from the mixture of solvent and eluted organic compound. The improvement in the process comprises eluting the organic compound from the carbon by applying vapors of the volatile solvent to a bed of the carbon maintained at a temperature at or slightly below the condensation temperature of the solvent, at a rate of less than about one-half bed volume per hour, until the volatile solvent is detected in the eluate. Then elution is continued until about one-half additional bed volume of eluate is collected which contains a concentrated aqueous solution of the organic compound in the volatile solvent. Volatile solvent is then evaporated to obtain an aqueous solution of the organic compound containing at least about 30% of the organic compound by weight.

DETAILED DESCRIPTION OF THE INVENTION

The process of this invention is suitable for the concentration of a variety of organic compounds from dilute aqueous solutions. It can be used to concentrate any organic compound which is readily adsorbed from solution by activated carbon and which can be desorbed by vapors of a volatile solvent. It is suitable for the concentration of dilute solutions of acetic acid, butanol, lactic acid, and ethanol. It is particularly suitable for extraction of these compounds from fermentation broths where they are produced by microorganisms.

Any activated carbon can be used as an adsorbent, provided that it adsorbs practical amounts of the organic compound from dilute aqueous solution. It is preferably a granular or beaded carbon of a mesh size that permits good flow of liquids through a bed of the carbon. Suitable carbons are CPG carbon, a granular carbon available from PPG Industries, Nuchar NW-40, a granular carbon available from the Westvaco Chemical Corporation, and G-BAC, a beaded carbon available from Union Carbide Corporation.

The organic compound is adsorbed from solution by mixing the solution with the adsorbent carbon. A convenient method for carrying out this process is to place the carbon in a column. The dilute solution of the organic compound is then added to the top of the column and allowed to flow through the column by gravity. Alternatively, the material can be adsorbed by passing the solution upward through the column. The process is continued until the carbon is saturated or nearly saturated with the organic compound. Once the material has been adsorbed on the carbon, excess water and unadsorbed material is allowed to drain from the column. Passage of air or an inert gas downward through the column can be used to increase the drainage rate and remove some additional water from the carbon.

Following the drainage step, a mixture of water and the organic compound is held by the carbon. Elution is accomplished by passing the vapors of a volatile solvent through the carbon. This step is conveniently carried out by passing vapors of the volatile solvent in at the top of a column containing the carbon with adsorbed material. The solvent vapors condense in the column and pass from the bottom of the column as a liquid.

In conducting the elution step, the column is maintained at or slightly below the condensation temperature of the volatile solvent. This means that the column temperature is between about 10° C. below, preferably about 5° C. below, the boiling point and the boiling point of the volatile solvent. The column is maintained at the desired temperature by means of a heated jacket or similar device and by the latent heat of vaporization given up by the condensing vapor.

A number of volatile solvents can be used in the process of this invention. It is preferred to use a solvent that distills at a temperature sufficiently below the boiling point of the organic material being desorbed to permit separation of the solvent by distillation. A solvent with a low specific heat and a low heat of vaporization is particularly desirable. Furthermore, the solvent should be one that does not react with the organic compound and that does not form an azeotrope with the organic compound. It is also preferred to use a volatile solvent which has a high degree of polarity. A solvent which is most preferred for use in this process is acetone. Other suitable solvents include diethyl ether, ethyl acetate, isopropyl alcohol, methanol and 2-butanone.

During the elution step, the vapors of the volatile solvent are passed through the carbon, maintained at the desired temperature, at such a rate that the solvent condenses before it leaves the carbon column. At first, the rate at which the vapors are added to the column is adjusted so that less than 0.5, preferably about 0.2 to 0.5, bed volumes per hour (BVH) of eluate is collected. This rate of flow is maintained at least until the volatile solvent is detected in the eluate. The first fraction eluted is mainly water. This greatly increases the concentration of the organic compound in the material still adsorbed on the carbon.

There is an additional advantage of the present process when it is used to recover products from fermentations. The first eluted fraction is pure enough so that it can be recycled directly to the fermentor or reactor from which it came. This reduces the amount of fresh water needed and the amount of wastewater produced by the process.

After the first fraction is eluted, the rate of flow of solvent vapor can be increased to about 1.0 BVH, if desired, to accelerate the rate of desorption. The second portion of eluate contains a mixture of organic compound, water and volatile solvent. After about an additional one-half bed volume of this mixture is collected, elution is stopped. The effluent mixture is now a concentrated aqueous solution of the organic compound in the volatile solvent. Up to about 96% of the water originally associated with the organic compound has been removed without water distillation, thereby saving the energy cost of this expensive process. The solvent then can be distilled from the effluent mixture and recovered for reuse. The residue, after solvent removal, is an aqueous solution containing at least about 30% of the organic compound by weight. If the original solution contained 5% or more of the organic compound, the residue will contain from about 40% to about 50% of the organic compound by weight.

Thus, it is possible to concentrate a dilute aqueous solution of an organic compound to a concentration of about 30% or greater. Furthermore, the energy requirements of the process are low when the preferred solvent, acetone, is used due to the low boiling point, low specific heat and small latent heat of vaporization of this solvent. The process is particularly suitable for the concentration of organic compounds produced by fermentation such as acetic acid and butanol.

The carbon can be regenerated after elution by passing steam through it to remove solvent. Carbon so regenerated after acetone elution regains its original adsorptive capacity. It can be reused many times.

The procedure of this invention is further illustrated by the following examples in which all parts and percentages are by weight unless expressly stated to be otherwise.

EXAMPLE 1

In a jacketed column of 2.2 cm internal diameter was placed 70 g (185 ml bed volume) of CPG carbon, a granular carbon available from the Pittsburgh Plate Glass Company. The carbon was saturated with a 5% acetic acid solution at pH 4.8. Twelve grams of acetic acid was adsorbed by the carbon. After adsorption was complete, the carbon column was drained and additional water was removed by passing an air stream downward through the column. The column was then heated to a temperature of between 50° and 60° C. before acetone vapor was passed in at the top of the carbon column. The effluent was removed from the bottom of the column. The first 50-ml fraction contained 2.33 g of acetic acid and 47.2 g water by weight. A second fraction (45 ml) contained 8.86 g of acetic acid and 8.05 g water by weight. The third fraction (50 ml) contained 0.87 g of acetic acid and 2.15 g water by weight. A final 50-ml fraction contained only 0.12 g of acetic acid.

This example illustrates that acetone vapor first displaces nonadsorbed feed liquor from a carbon column which has been saturated with aqueous acetic acid. Then the main amount of adsorbed acetic acid is eluted. This second eluate on evaporation of the acetone leaves an aqueous acetic acid solution containing nearly 50% acetic acid. The process is thus seen to be suitable for the rapid concentration of a solution of acetic acid.

EXAMPLE 2

The process of Example 1 was repeated except that the temperature of the column during desorption was maintained carefully within a narrow temperature range and the carbon was saturated with 7.5% acetic acid solution at pH 2.5. Experiments were run in which the temperature of the column was maintained at 51° C., 53° C., 56° C. and 60° C. When the columns were maintained at 51° C., 53° C. and 56° C., all of the acetic acid adsorbed on the column was eluted in the first 200 ml of eluate. However, when the column was held at a temperature of 60° C., only 77% of acetic acid was eluted in the first 200 ml of eluate.

This indicates that the column should be held at or slightly below the condensation temperature of the acetone vapor (56° C.) in order for the rapid elution of the acetic acid to occur.

EXAMPLE 3

In a jacketed column of 2.2 cm internal diameter was placed 70 g (180 ml bed volume) of Nuchar HW-40, a granular carbon available from the Westvaco Chemical Corporation. The carbon was saturated with a 10% acetic acid solution at pH 4.8. After adsorption was complete, the carbon column was drained and additional water was removed by passing an air stream downward through the column. The column was then heated to a specified temperature before acetone vapor was passed in at the top of the carbon column. The effluent was removed from the bottom of the column. Four fractions of approximately 25 ml, 20 ml, 50 ml and 50 ml respectively were collected. The contents of each fraction were analyzed for acetic acid and water. Results of experiments run at various temperatures between 30° C. and 55° C. are reported in Table I.

TABLE I
ELUTION OF ACETIC ACID FROM NUCHAR HW-40 CARBON

| Column Temp (°C.) | Fraction 1 Acetic Acid (%) | Fraction 1 Water (%) | Fraction 2 Acetic Acid (%) | Fraction 2 Water (%) | Fraction 3 Acetic Acid (%) | Fraction 3 Water (%) | Fraction 4 Acetic Acid (%) | Fraction 4 Water (%) |
| --- | --- | --- | --- | --- | --- | --- | --- | --- |
| 30 | 2.94 | 88.66 | 12.54 | 75.49 | 15.18 | 18.83 | 3.06 | 2.46 |
| 30 | 2.52 | 92.11 | 12.24 | 77.60 | 15.12 | 17.28 | 2.88 | 1.77 |
| 40 | 3.48 | 89.92 | 9.9 | 81.92 | 17.76 | 20.94 | 3.3 | 1.87 |
| 40 | 3.78 | 88.44 | 6.1 | 86.72 | 19.68 | 23.79 | 3.3 | 2.37 |
| 50 | 4.14 | 88.27 | 10.38 | 80.39 | 17.94 | 18.42 | 2.76 | 1.78 |
| 50 | 4.26 | 89.20 | 6.42 | 88.67 | 20.82 | 21.10 | 2.76 | 1.04 |
| 53 | 2.52 | 90.11 | 8.76 | 84.35 | 18.54 | 17.76 | 2.94 | 1.50 |
| 54 | 3.42 | 91.1 | 5.25 | 90.51 | 20.11 | 21.63 | 2.94 | 1.24 |
| 54 | 4.02 | 88.38 | 5.46 | 86.2 | 20.64 | 21.70 | 2.58 | 0.89 |
| 54 | 3.54 | 90.56 | 4.86 | 87.8 | 21.6 | 22.47 | 2.7 | 0.87 |
| 55 | 3.36 | 89.59 | 3.54 | 89.54 | 19.38 | 22.47 | 2.4 | 2.19 |
| 55 | 3.54 | 89.01 | 4.2 | 87.8 | 19.92 | 26.8 | 2.7 | 1.23 |

When the temperature of the column is held at 30° C. or 40° C. by means of cooling water in the jacket, the acetone vapor is condensed so rapidly at the elution rate used that channeling tends to occur and separation of the water in the first two fractions is less complete. When the temperature of the column is maintained between 50° C. and 55° C. during the elution, the bulk of the water is eluted in the first two fractions and the adsorbed acetic acid is eluted in the last two fractions. When the column temperature is maintained at 50° to 55° C., Fractions 3 and 4, which contain over 95% of the adsorbed acetic acid, can be combined to give acetic acid solutions which, after removal of acetone, consist of approximately 50% aqueous solutions of acetic acid.

COMPARATIVE TEST

The procedure of Example 1 was repeated except that Nuchar NW-40 was used as the adsorbent and elution was accomplished using liquid acetone at 54°-55° C. The temperature of the column was maintained at 54°-55° C. during elution. Again, the acetic acid was eluted in the first 200 ml of eluate—mainly in the second 50-ml fraction. However, this fraction on an acetone-free basis was an aqueous solution containing only about 35% acetic acid. This comparative test demonstrates that a much less concentrated aqueous acetic acid solution is obtained when acetone liquid rather than acetone vapor is applied to the column to elute the acid.

EXAMPLE 4

The carbon column described in Example 3 was saturated with a 2.5% acetic acid solution at pH 4.8. After adsorption was complete, the carbon column was drained and additional water was removed by passing an air stream downward through the column. The column was heated to 54° C. before acetone vapor was passed in at the top of the column. The effluent was removed from the bottom of the column. Four fractions of approximately 50 ml each were collected. The first fraction (average of 3 runs) contained 96.5% water and only 1.43% acetic acid. Combined Fractions 2 and 3 (average of 3 runs) contained 13.5% acetic acid and 21.0% water. Only traces of acetic acid were present in Fraction 4.

This example demonstrates that a 39% acetic acid solution can be obtained from a 2.5% acetic acid solution (pH 4.8) by this process, which removes about 96% of the water originally associated with this acetic acid.

EXAMPLE 5

The procedure of Example 4 was repeated except that the carbon column was saturated with a 1.25% acetic acid solution at pH 4.8. Again, the bulk of the acetic acid was recovered in Fractions 2 and 3 which, after combining and subtracting the acetone, give a 34% aqueous solution of acetic acid. This process removes over 97% of the water originally associated with this acetic acid. This example further demonstrates the usefulness of this process for concentrating very dilute acetic acid solutions.

EXAMPLE 6

The experiment of Example 2 was repeated except that the carbon was saturated with 5% acetic acid solution at pH 2.5, methanol vapor (condensation temperature 65° C.) was used for the elution and the column temperatures were held at 61° C., 66° C. and 70° C. respectively. A quantitative elution of acetic acid was achieved only when the temperature was at 61° C. When the temperature were at 66° C. and 70° C., acetic acid recoveries of 78% and 61.5% respectively were observed.

These tests further emphasize the importance of conducting the elution of the acetic acid at a temperature at or slightly below the condensation temperature of the vapor of the eluting solvent.

EXAMPLE 7

The procedure of Example 4 was repeated using a 5% acetic acid solution at pH 4.8 except that the eluate was isopropyl alcohol vapor (condensation temperature 82° C.) and the temperature of the column was held at 80° C. during the elution. Analysis of the eluate was as follows:

| Fraction | Volume (ml) | Acetic Acid (g) | Water (%) |
|---|---|---|---|
| 1 | 40 | 1.85 | 94.5 |
| 2 | 50 | 5.61 | 23.9 |
| 3 | 50 | 0.60 | 2.1 |
| 4 | 50 | 0.12 | 1.2 |

EXAMPLE 8

The elution procedure of Example 7 was repeated except that the eluate was ethyl acetate vapor (condensation temperature 77° C.) and the temperature of the column was held at 70° C. during the elution. Analysis of the eluate is as follows:

| Fraction | Volume (ml) | Acetic Acid (g) | Water (%) |
|---|---|---|---|
| 1 | 25 | 1.94 | 88.3 |
| 2 | 20 | 2.54 | 14.5 |
| 3 | 50 | 3.75 | 8.8 |
| 4 | 50 | 1.71 | 6.5 |
| 5 | 50 | 0.63 | 4.7 |

EXAMPLE 9

The elution procedure of Example 7 was repeated except that 2-butanone vapor (condensation temperature 80° C.) was used as the eluate and the column was held at 76° C. Analysis of the eluate was as follows:

| Fraction | Volume (ml) | Acetic Acid (g) | Water (%) |
|---|---|---|---|
| 1 | 25 | 1.85 | 92.8 |
| 2 | 20 | 4.08 | 64.2 |
| 3 | 50 | 4.26 | 16.2 |
| 4 | 50 | 0.60 | 4.3 |

Examples 6, 7, 8 and 9 demonstrate the vapors of solvents other than acetone can be used in the process of this invention.

EXAMPLE 10

The elution procedure of Example 7 was followed except that diethyl ether vapor (condensation temperature 35° C.) was used as the eluate and the column was held at 34° C. during the elution. The first fraction of eluate separated into two layers which were analyzed separately. Analysis of the eluate was as follows:

| Fraction | Volume (ml) | Acetic Acid (g) | Water (%) |
|---|---|---|---|
| 1 | 50 (upper 30) | 1.82 | 4.2 |
|  | (lower 20) | 1.50 | 92.0 |
| 2 | 50 | 2.79 | 3.6 |
| 3 | 50 | 1.50 | 2.6 |
| 4 | 50 | 0.75 | 1.8 |
| 5 | 50 | 0.36 | 1.5 |

Ether vapor appears to be less satisfactory than the other eluates. Water is retained on the carbon longer when this solvent is used, and it is more difficult to remove the acetic acid.

EXAMPLE 11

The general procedure of Example 3 was followed except that 400 ml of a 5.1% solution of lactic acid was applied to the column and the temperature of the column was held at 54° C. during elution. Analysis of the eluate was as follows:

| Fraction | Volume (ml) | Lactic Acid (g) | Water (%) |
|---|---|---|---|
| 1 | 40 | 1.98 | 95.0 |
| 2 | 50 | 10.13 | 28.8 |
| 3 | 50 | 1.44 | 1.5 |
| 4 | 50 | 0.45 | 0.8 |

Combined Fractions 2 and 3, after evaporation of acetone, give an aqueous solution containing about 40% lactic acid. It is thus seen that the present invention is suitable for the concentration of a dilute lactic acid solution.

EXAMPLE 12

The general procedure of Example 3 was followed except that 400 ml of a clarified fermentation broth containing 8.3% ethanol was applied to the column, and the temperature of the column was held at 54° C. during elution. The broth was obtained by the fermentation of a starch hydrolyzate solution with the yeast *Saccharomyces cerevisiae*. The fermentation broth also contained 1.2% glycerol and 0.4% lactic acid. Analysis of the eluate was as follows:

| Fraction | Volume (ml) | Ethanol (%) | Water (%) |
|---|---|---|---|
| 1 | 25 | 9.6 | 90.4 |
| 2 | 15 | 13.0 | 87.0 |
| 3 | 50 | 13.5 | 19.8 |
| 4 | 50 | 0.1 | 1.8 |

This example demonstrates that the process of the present invention is suitable for concentrating the ethanol solution produced by a fermentation reaction.

EXAMPLE 13

The general procedure of Example 3 was followed except that 1750 ml of a crude fermentation broth containing 1.4% butanol and lesser amounts of acetone, ethanol and fatty acids was used and the temperature of the column was held at 54° C. during elution. This broth was obtained by the fermentation of a starch hydrolyzate solution by the bacterium *Clostridium acetobutylicum*. The broth also contained 4.9% carbohydrate. Analysis of the eluate was as follows:

| Fraction | Volume (ml) | Butanol (%) | Water (%) | Carbohydrate (%) |
|---|---|---|---|---|
| 1 | 25 | 1.3 | 84.0 | 7.0 |
| 2 | 15 | 13.9 | 57.3 | 6.5 |
| 3 | 50 | 17.7 | 22.5 | 1.5 |
| 4 | 50 | 2.6 | 2.8 | 0.2 |
| 5 | 50 | 0.1 | 0.8 | 0.1 |

In some parallel experiments, the second fraction separated into two layers with the upper layer containing more butanol and the lower layer containing more carbohydrate.

This example demonstrates that the process of this invention can be used to concentrate butanol obtained by fermentation even when the crude fermentation broth contains much unfermented carbohydrate material.

Thus, it is apparent that there has been provided, in accordance with the invention, a process for the concentration of dilute solutions of organic compounds that fully satisfies the objects, aims and advantages set forth above. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for concentrating a dilute aqueous solution of an organic compound which is readily adsorbed from solution by activated carbon and which can be desorbed by vapors of a volatile solvent by adsorbing the organic compound on an adsorbent carbon, eluting the organic compound from the carbon with a volatile solvent that distills at a temperature below the boiling point of the organic compound, and separating the volatile solvent from the mixture of solvent and eluted organic compound, wherein the improvement comprises applying vapors of the volatile solvent to a bed of the carbon, said bed being maintained at a temperature at or slightly below the condensation temperature of the solvent, at a rate of less than about one-half bed volume per hour until the volatile solvent is detected in the eluate, continuing to apply said vapors until about one-half bed volume of eluate containing a concentrated aqueous solution of the organic compound in the volatile solvent is collected, and evaporating the volatile solvent from said one-half bed volume of eluate to obtain an aqeous solution of the organic compound containing at least about 30% of the organic compound by weight.

2. The process of claim 1 wherein the adsorbent carbon is held in a column.

3. The process of claim 2 wherein the carbon column is regenerated by passing steam through the carbon column after eluting the organic compound from the carbon.

4. The process of claim 2 wherein the vapors of the volatile solvent are introduced into the top of the carbon column and the condensate is removed from the bottom of the column.

5. The process of claims 1, 2 or 4 wherein the volatile solvent is acetone.

6. The process of claim 5 wherein the carbon column is maintained at a temperature of from about 50° C. to about 56° C. during the elution.

7. The process of claim 5 wherein air is passed through the bed of carbon before the vapors of volatile solvent are passed through the bed of carbon.

8. The process of claim 5 wherein the eluate obtained before the volatile solvent is detected in the eluate is readsorbed on adsorbent carbon in a recycle process.

9. The process of claims 1, 2 or 4 wherein the volatile solvent is methanol.

10. The process of claim 9 wherein the carbon column is maintained at a temperature of from about 55° C. to about 63° C. during the elution.

11. The processes of claims 1, 2 or 4 wherein the volatile solvent is selected from the group consisting of 2-butanone, ethyl acetate, isopropyl alcohol, and diethyl ether.

12. The process of claim 1 wherein the organic compound is acetic acid.

13. The process of claim 12 wherein the dilute aqueous acetic acid solution is a fermentation broth obtained by cultivating an acetic acid-producing microorganism.

14. The process of claim 1 wherein the organic compound is butanol.

15. The process of claim 14 wherein the dilute aqueous butanol solution is a fermentation broth obtained by cultivating a butanol-producing microorganism.

16. The process of claim 1 wherein the organic compound is ethanol.

17. The process of claim 16 wherein the dilute aqueous ethanol solution is a fermentation broth obtained by cultivating an ethanol-producing microorganism.

18. The process of claim 1 wherein the organic compound is lactic acid.

19. The process of claim 18 wherein the dilute aqueous lactic acid solution is a fermentation broth obtained by cultivating a lactic acid-producing microorganism.

* * * * *